US006328966B1

(12) United States Patent
Pierpaoli

(10) Patent No.: US 6,328,966 B1
(45) Date of Patent: *Dec. 11, 2001

(54) TRANSFERRIN COMPOSITIONS TO ALLEVIATE THE SIDE EFFECTS OF CYTOTOXIC DRUGS

(75) Inventor: Walter Pierpaoli, Gudo (CH)

(73) Assignee: I.S.I.S.P.A., Lucca (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/899,140

(22) Filed: Jul. 23, 1997

Related U.S. Application Data

(63) Continuation of application No. 08/624,524, filed as application No. PCT/EP95/03191 on Aug. 11, 1995, now abandoned.

(30) Foreign Application Priority Data

Aug. 11, 1994 (EP) ................................. 94401847

(51) Int. Cl.[7] ............. A61K 39/00; A61K 38/12; A01N 37/18; C07K 1/00
(52) U.S. Cl. ............. 424/184.1; 514/2; 530/317; 530/350; 530/394; 530/400
(58) Field of Search ............... 514/2; 530/350, 530/394, 400, 317; 424/184.1

(56) References Cited

U.S. PATENT DOCUMENTS

| 4,590,001 | * | 5/1986 | Stjeruholm . |
| 5,108,987 | * | 4/1992 | Faulk . |
| 5,236,899 | * | 8/1993 | Durette .................. 514/11 |
| 5,252,715 |   | 10/1993 | Haupt . |

FOREIGN PATENT DOCUMENTS

| 426924 | 5/1991 | (EP) . |
| 568200 | 11/1993 | (EP) . |
| 9007861 | * 7/1990 | (WO) . |

OTHER PUBLICATIONS

Hird et al, Genes & Cancer, 1990, John Wiley & Sons, NY pp. 183–189.*
Dorland's Med. Dicitionary, 1985, WB Saunders Co, Philadelphia pp. 472 & 522.*
Goodman and Gilman (The pharmaceutical Basis of Therapeutics, 6th Edition, MacMillan Publishing Co., NY, p. 711, 1980.*
Kennedy et al (J. Clin. Invest., 85:1565–1573), 1990.*
Ahmed et al (J. Am. Acad. Derm., 11:1115–11126), 1984.*

* cited by examiner

Primary Examiner—Susan Ungar
(74) Attorney, Agent, or Firm—Birch, Stewart, Kolasch & Birch, LLP

(57) ABSTRACT

The invention pertains to eutrophic drug composition containing transferrins, particularly human transferrins. This composition allows the toxic effects of cytotoxic drugs such as cyclosporin when used at high dosages or over a prolonged period of time to be alleviated or suppressed.

5 Claims, 9 Drawing Sheets

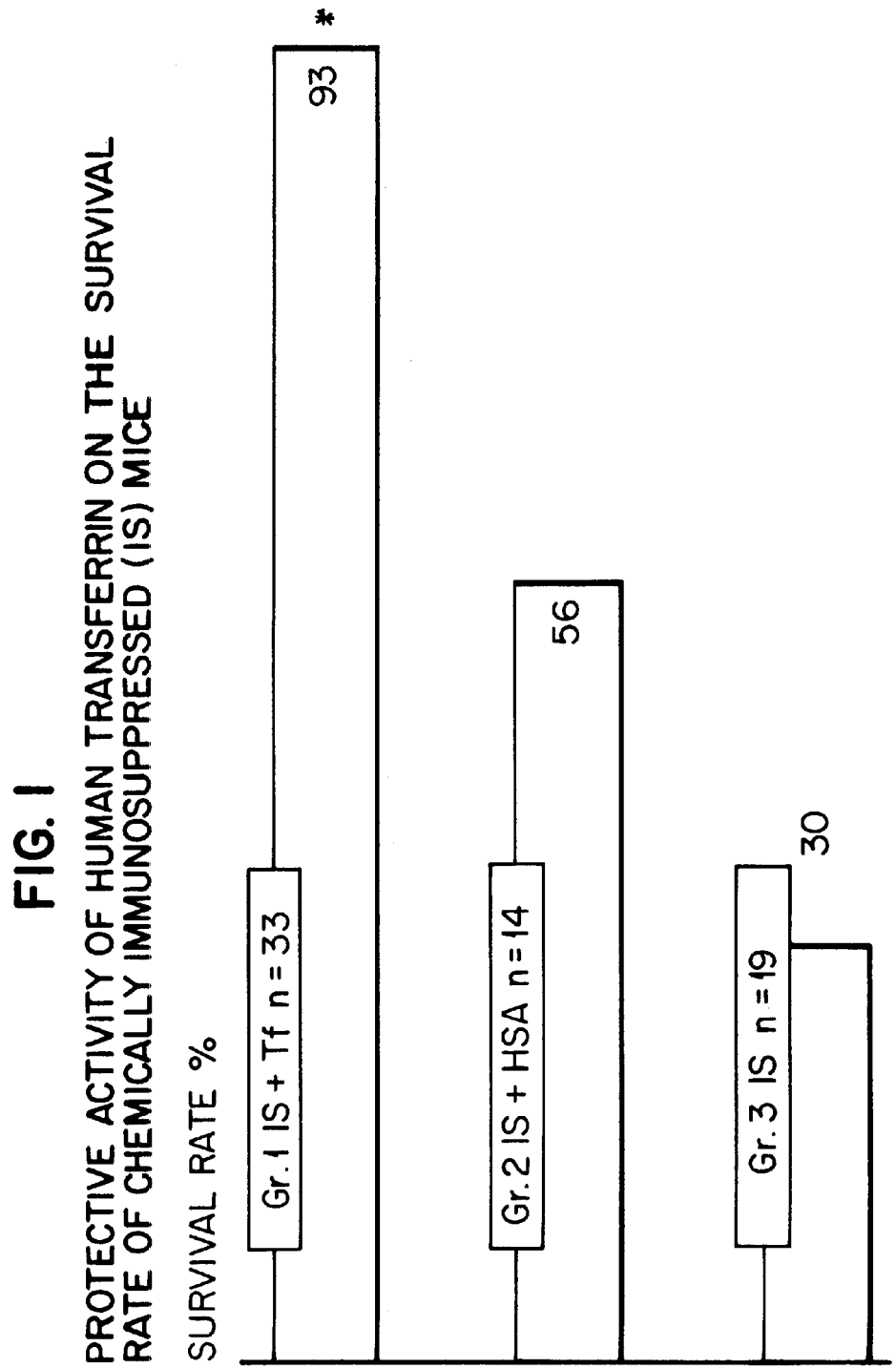

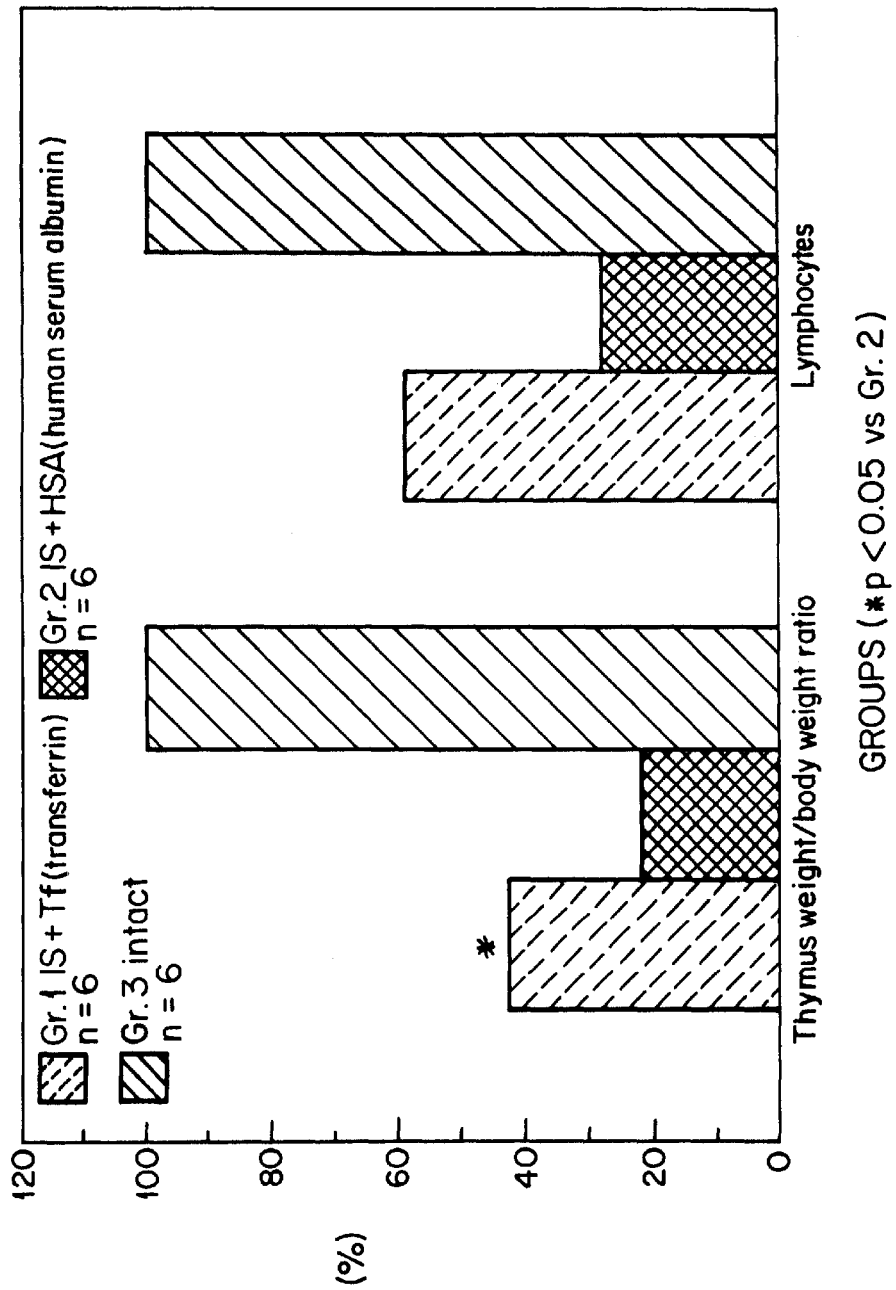

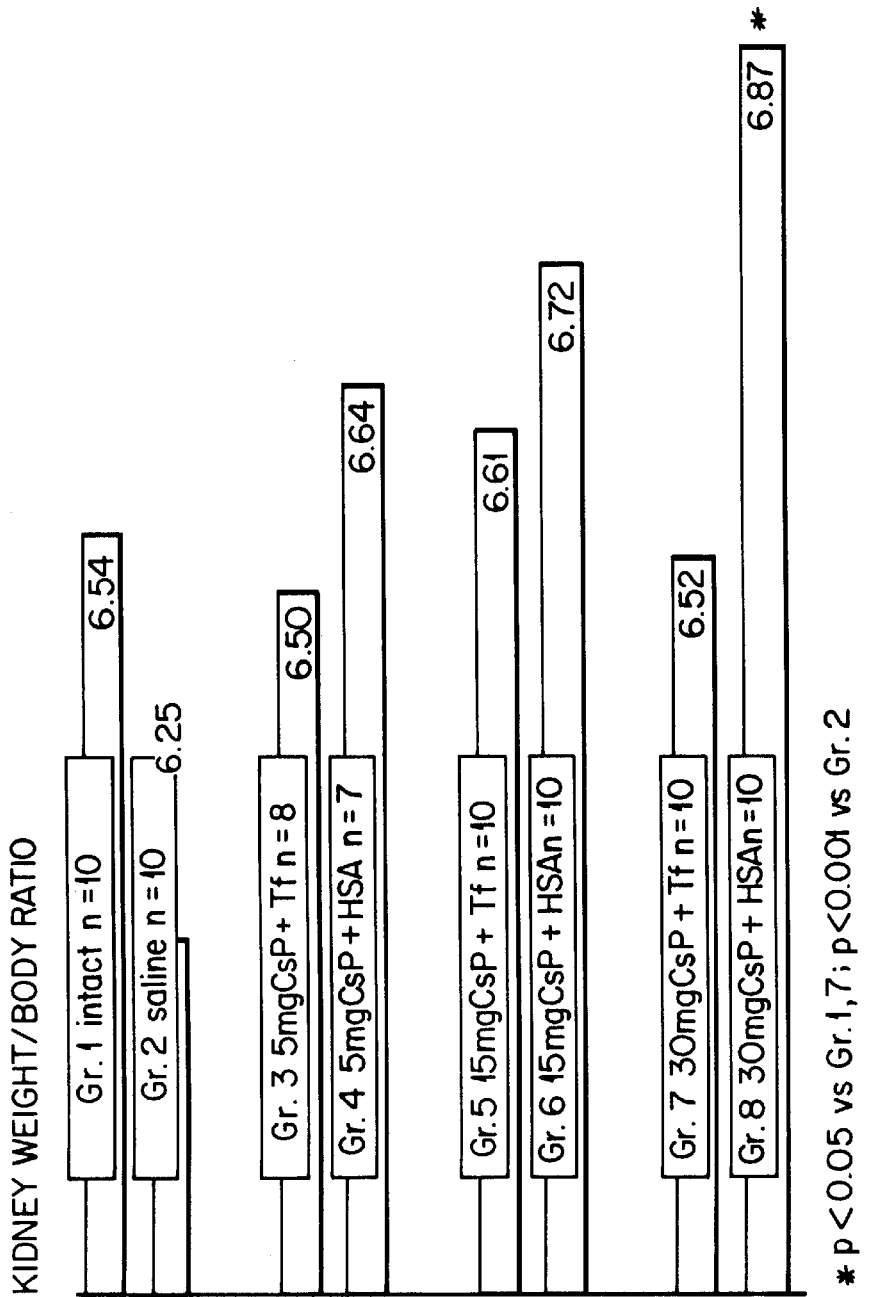

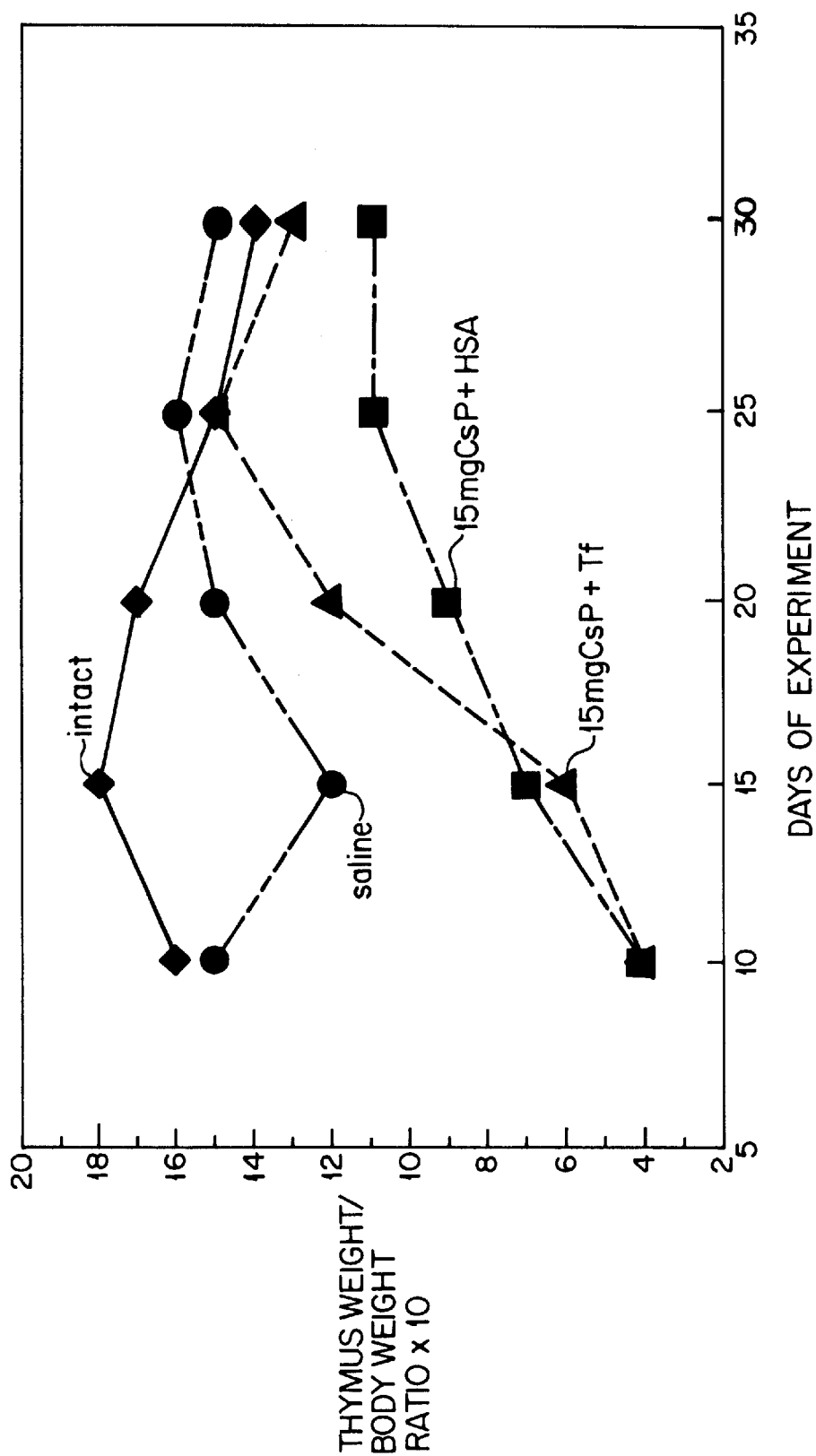

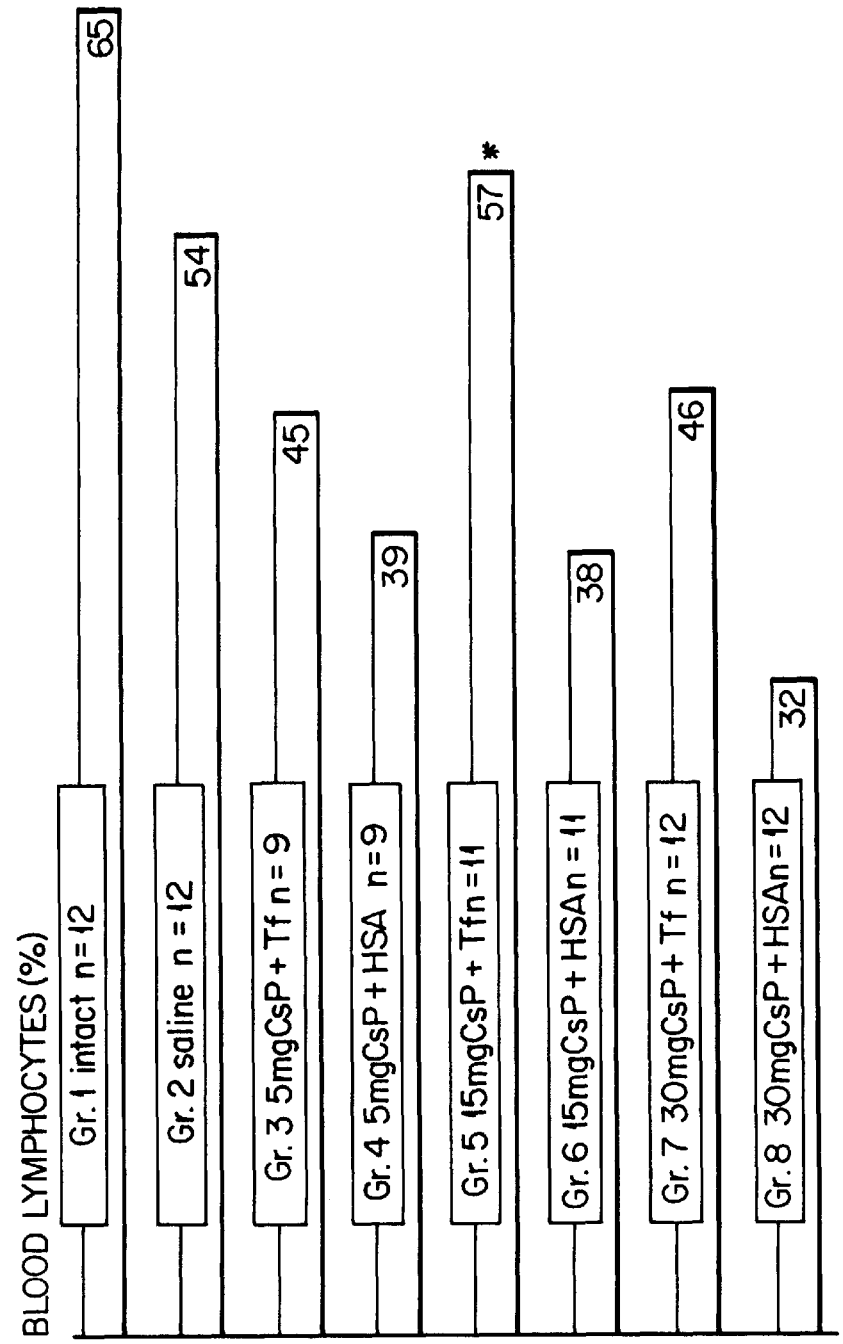

TRANSFERRIN COMPOSITIONS TO ALLEVIATE THE SIDE EFFECTS OF CYTOTOXIC DRUGS

This application is a continuation of application Ser. No. 08/624,524, filed Aug. 5, 1996, now abandoned, which is a 371 of PCT/EP95/03191 filed Aug. 11, 1995.

BACKGROUND OF THE INVENTION (i) Field of the Invention

The invention relates to the production of new drugs, particularly eutrophic drugs, the active principle of which consists of transferrins. The invention is of particular significance for human therapy. However it is not limited thereto. It may also be applicable in veterinary medicine.

(ii) Description of Related Art

An eutrophic drug means a drug that is capable of maintaining or restoring the structure and function of tissue and cells in the person's body, particularly when that person undergoes treatments with other drug principles which beyond the favourable clinical effects which they may exert, are also fraught with undesirable side effects, particularly are liable of seriously injuring healthy cells and tissue of the body. Thus no matter how valuable the drug, difficulties may be encountered in monitoring its use in patients heavily in need for it. Such type of drugs shall hereinafter be referred to as "cytotoxic drugs".

An example of such cytotoxic drugs is cyclosporin which, as is well known, can also induce in the treated host muscular and functional disabilities accompanied by severe pains and/or nephrotoxicity that can ultimately produce renal dysfunction in the patient, for instance as evidenced by falls in glomerular filtration rates.

The dramatic side effects of antitumor drugs are well known. Similarly, anti-inflammatory drugs can entail a full array of damages ranging from gastric diseases to general disturbance of the metabolism in the treated patient.

There is thus a strong need to for a drug composition capable of overcoming the side effects of cytotoxic drugs, particularly to either prevent the tissue or cell degradation or promote the repair of damaged cells and tissue, more generally of assisting the natural principles which in the body participate to the eustasis.

The eutrophic drug of the composition of the invention is characterized in that its active principle consists of transferrins.

Although not always compulsory, the transferring should originate from the same mammal as the treated one. Thus human transferring should be the preferred active principle of eutrophic drugs for use in man.

Transferrins as such are a class of two-sited, single chain, metal-binding proteins, widely distributed in physiological fluids and cells of vertebrates.

Each transferrin consists of a single polypeptide chain, of molecular weight in the range 76000–81000, which contains two similar but not identical binding sites.

If the shape of human serum transferrin is approximated by an ellipsoid of revolution, then the ratio of major radii to minor is 2:1 for iron-saturated transferrin, and increases to 2.5:1 or 3:1 when the protein is freed from iron.

The isoelectric point of serum transferrin is on the acid side of neutrality.

The transferring are all glycoproteins.

Human serum transferrin contains about 5% carbohydrate, linked to the protein in two identical and nearly symmetrical branched heterosaccharide chains. it has a molecular weight of about 80000. 1 mg of the iron-saturated protein contains about 1.4 $\mu$g iron.

The complete amino acid sequence of human plasma transferrin has been established by at least three groups using CNBr cleavage (CNBr) and by complementary DNA (cDNA) methods (MacGillivray, RTA, et al. "The complete amino acid sequence of human serum transferrin", Proc. Natl. Acad. Sci. USA 79, 2504–2508, 1982 and Uzan G. et al. "Molecular cloning and sequence analysis of cDNA for human transferrin" Biochem. Biophys. Res. Commun. 1990, 273–281, 1984 and Yang F. et al. "Human transferrin: cDNA characterization and chromosomal localization" Proc. Natl. Acad. Sci. USA 81, 2752–2756, 1984). It is composed of 678 amino acid residues, which together with the two-N-linked oligosaccharide chains exhibit a calculated molecular weight of 79,570 (of which 6% is contributed by the glucosidic moiety: MacGillivray, RTA et al. and Uzan G. et al., "Molecular cloning and sequence analysis of cDNA for human transferrin" Biochem. Biophys. Res. Commun. 119, 273–281, 1984). Williams J. ("The evolution of transferrin", Trends Biochem. Sci. 7, 394–397, 1982) has suggested the importance of sulfhydryl groups in stabilizing the iron-binding site and has traced their evolutionary developement to the 17 disulfides found in human transferrin.

For a general review of the status of general knowledge about transferrins see the general publication titled "The physiology of transferrin and transferrin receptors" by Helmut A. Huebbers and Clement A. Finch in Phyiological Reviews, vol. 67, n° 2, Apr. 1987.

Procedures for obtaining transferrin, particularly transferrin of human origin in a biologically pure state have been disclosed in that publication. Preferred purification procedures are either based on physico-chemical based separation steps followed by selective fixation on matrix-bound antibody or matrix-bound receptor.

SUMMARY AND OBJECTS OF THE INVENTION

In a preferred embodiment of the invention, the transferrins used for the purpose of the invention consist of a mixture of transferrins obtained from a sufficient. number of donors. Advantageously, one uses "pools" of transferring, as they are obtainable from plasma pools produced in industry which can originate from several hundreds to several thousands of donors. As a matter of fact, it is believed that transferring obtained from different individual persons may have varying effects on the recipient, depending on their respective degrees of genetic similarities with said recipient. Advantageously, the transferrins for use in this invention result from the purification product obtained from a plasma resulting from the pooling of plasmas obtained from blood of at least 1000 donors.

The invention finds particularly advantageous uses in the protection of persons subjected to an immunosuppressive treatment, particularly with cyclosporin or other more or less related immunosuppressive drugs, e. g. FK506 and rapamycin. As a matter of fact, transferrins have been found to efficiently counteract the toxic effects of such drugs, as this will be further illustrated hereafter by the eustatic or eutrophic effect of transferrins on different metabolic functions in animals subject to treatments with cyclosporin, when they are either prolonged or carried out with high dosages.

As this will be seen hereafter, the results obtained at the histological level are spectacular. As well known the organs which are susceptible to the toxic effects of chronic administration of cyclosporin are particularly targetted on the thymus and even more so on the kidneys.

Transferrins are of particular interest in association with cyclosporin or other drugs having similar immunosuppressive effects, allowing for instance the graft of cells or tissue of a donor host in an allogeneic, or even xenogeneic recipient to succeed. As a matter of fact, transferrins are by themselves capable of inducing similar immunosuppressive effects under similar conditions in the recipient host, particularly for preventing graft-rejection, when administered together or concurrently with the grafting of the cells, tissue or organs in the recipient.

The invention however is not limited thereto.

The transferring can also be used to combat the toxic effects of other cytotoxic agents or compounds, particularly of those known to induce kidney damage to be substantially diminished, let alone eliminated. By way of example of such other drugs, one may mention:

antibiotics, particularly Polyene antibiotics, such as Colimycin and Gentamycin;

non-steroid anti-inflammatory drugs, particularly Ibuprofen;

anti-tumor drugs, such as Cis-platinum, or other immunosuppressive and cytotoxic drugs like Prednisolone or cyclophosphamide.

As already mentioned, the invention is not restricted to the use of transferrins in association with drugs which target principally the kidneys. Transferrins can also be used to prevent the damage of other tissues, for instance for the sake of preventing ear damages often produced by Gentamycin, Cis-platinum or streptomycin, by way of examples, in a number of patients.

The compositions of the invention are further not limited to the use of transferring in association with a cytotoxic drug. Their use can be extended to other forms of therapy, e. g. radiotherapy in the case of cancer. Their use is all the more beneficial as particularly natural transferrins are fully devoid of toxicity.

It goes however without saying that the invention is not limited to the use of natural transferrins for the above discussed purposes. Recombinant transferrins obtained by genetic engineering techniques, or fragments thereof, to the extent where they retain the suitable biological activites, for instance those illustrated in the examples which follow, can be applied too.

Whatever the nature of the cytotoxic therapeutical compound or agent used, it will be appreciated that transferring will then enable limitations in dosage or in duration of the treatments to be overcome, thereby providing for a full beneficial effect of the "cytotoxic drug" administered, with a concommitant reduction, let alone suppression of the mentioned side effects.

The amounts of the transferring to be administered will vary to a considerable extent depending upon the nature of the cytotoxic drug with which it is to be associated. Simply for the purpose of giving non-limitative examples, daily administrations of transferrin in a human should range normally from 2 mg to 10 mg/kg of body weight, particularly when injected intravenously, or from 5 mg to 50 mg/kg of body weight when injected intramuscularly. Obviously, the dosages retained should be left with the clinician. They may also vary according to the dosages of the cytotoxic drugs which are selected by the clinician.

Generally speaking the invention further relates to compositions containing both the transferring and the cytotoxic drug. It will readily appear to the person skilled in the art that two principles may be administered either in admixture or sequentially at alternate times.

Further possibilities of the invention will further appear for the person skilled in the art upon reading the examples which follow, such description being further supported by the drawings in which:

BRIEF DESCRIPTION OF THE DRAWINGS

FIG. 1 illustrates the protective activity of human transferrin on the survival rate of chemically immunosuppressed (IS) groups (Gr.) of mice (expressed as survival rate % as compared to non-immunosuppressed controls)

n=number of animals in the respective groups
*$p<0.001$ vs Gr. 3; $p<0.01$ vs Gr. 2

FIG. 2 illustrates the capability of human transferrin to prevent thymus involution and lymphopenia in chemically immunosuppressed (IS) mice. The results are expressed as the variation in percentage of the ratio of thymus weight (tw) to body weight (bw) in the different immunosuppressed groups as compared to non-immunosuppressed controls.

tw=thymus weight
bw=body weight
Tf=transferrin
HSA=human serum albumin
*$p<0.05$ vs Gr. 2

FIG. 3 illustrates the capability of human transferrin (Tf) to prevent kidney damage in mice chronically treated with cyclosporine (CsP)
*$p<0.05$ vs Gr. 1.7; $p<0.001$ vs Gr. 2

FIG. 4 shows that human transferrin corrects the toxic effect of cyclosporine in chronically treated mice. The results are expressed graphically as variation of the thymus weight/body weight ratio×10 (on the axis of ordinates) as a function of the length of the experiment expressed in days (on the axis of abscissae) in the different groups of animals.

FIG. 5 shows that human transferrin prevents lymphopenia in mice chronically treated with cyclosporine. Results are expressed as percentages of reduction of lymphocytes as compared to controls.

Figure 6A:
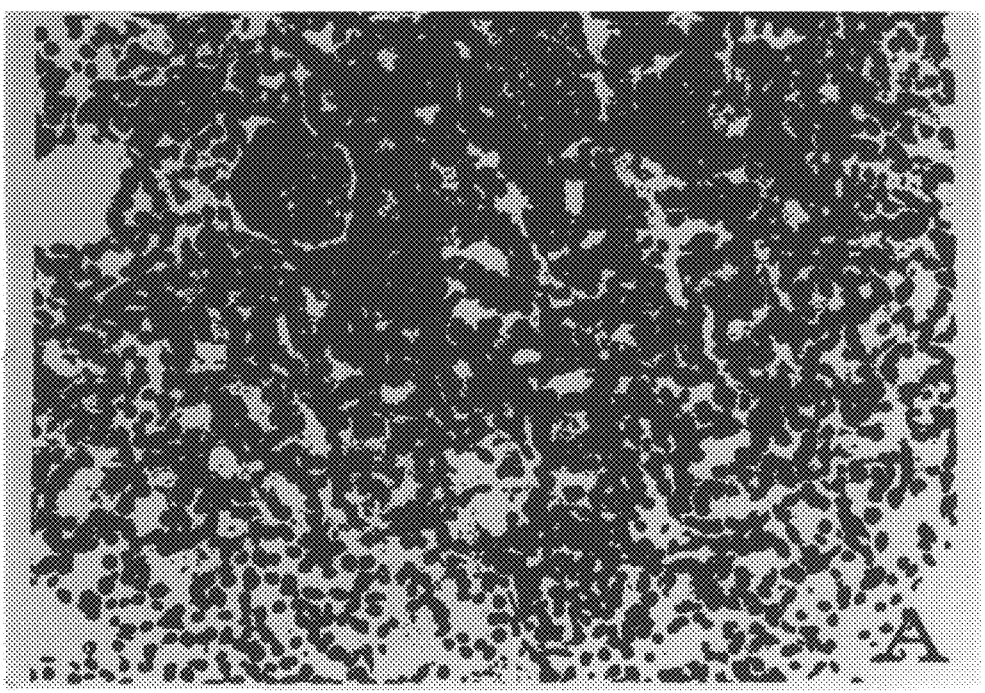
Figure 6B:
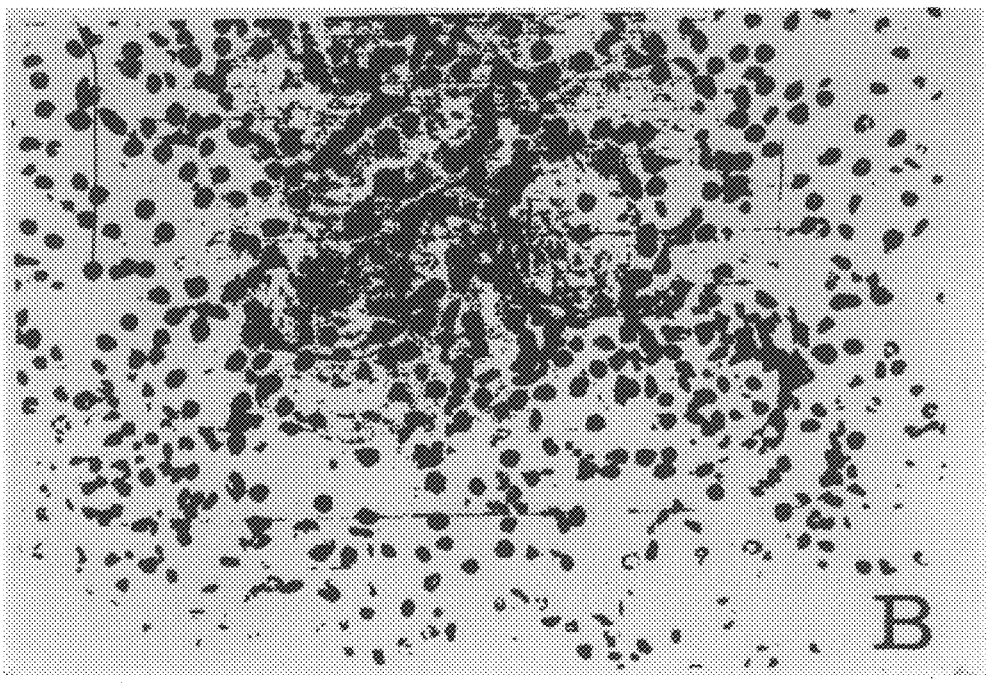
Figure 6C:
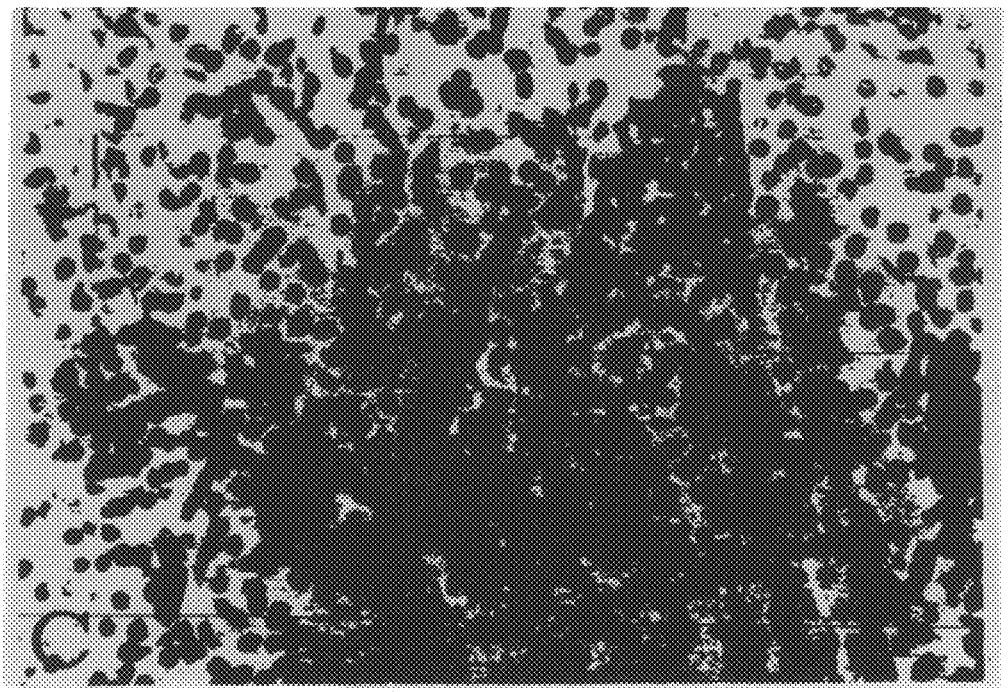
Figure 6D:
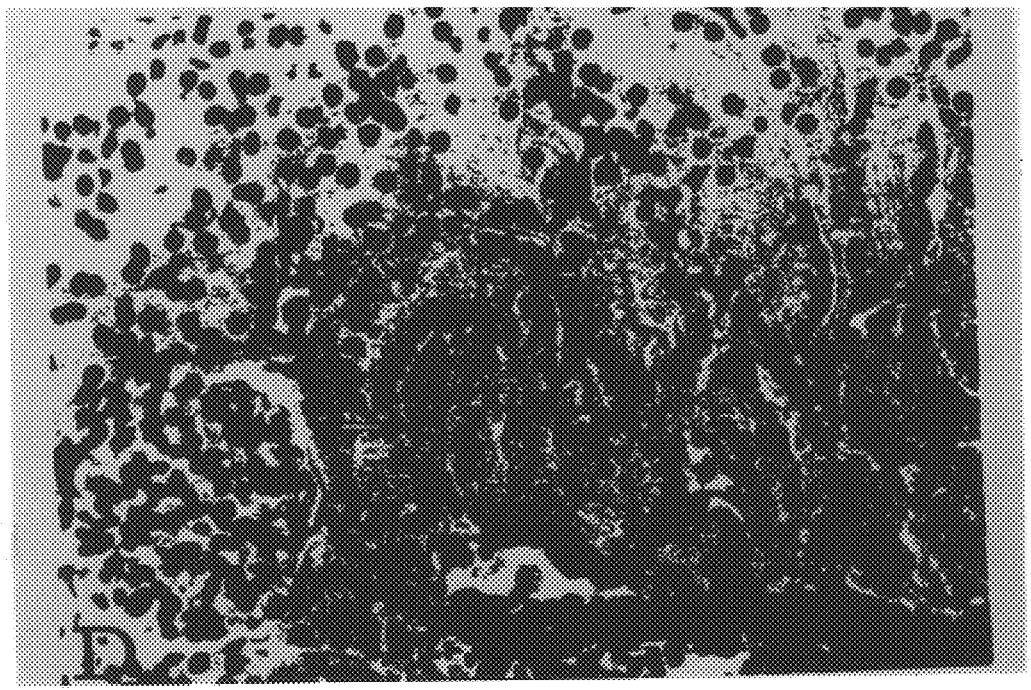
Figure 6E:
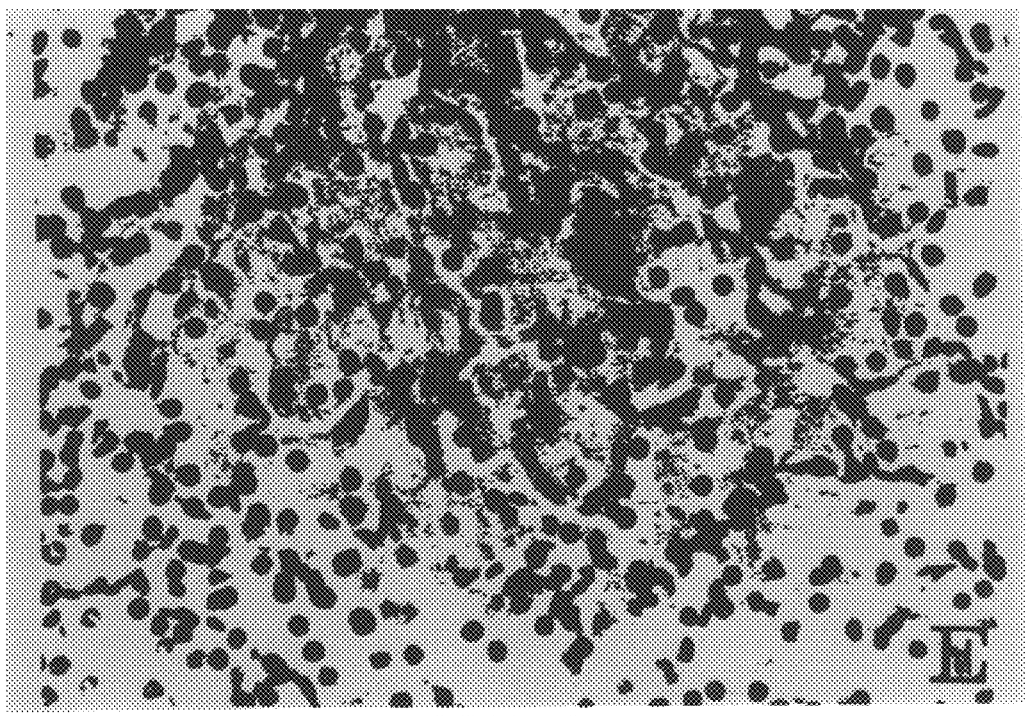
Figure 6F:
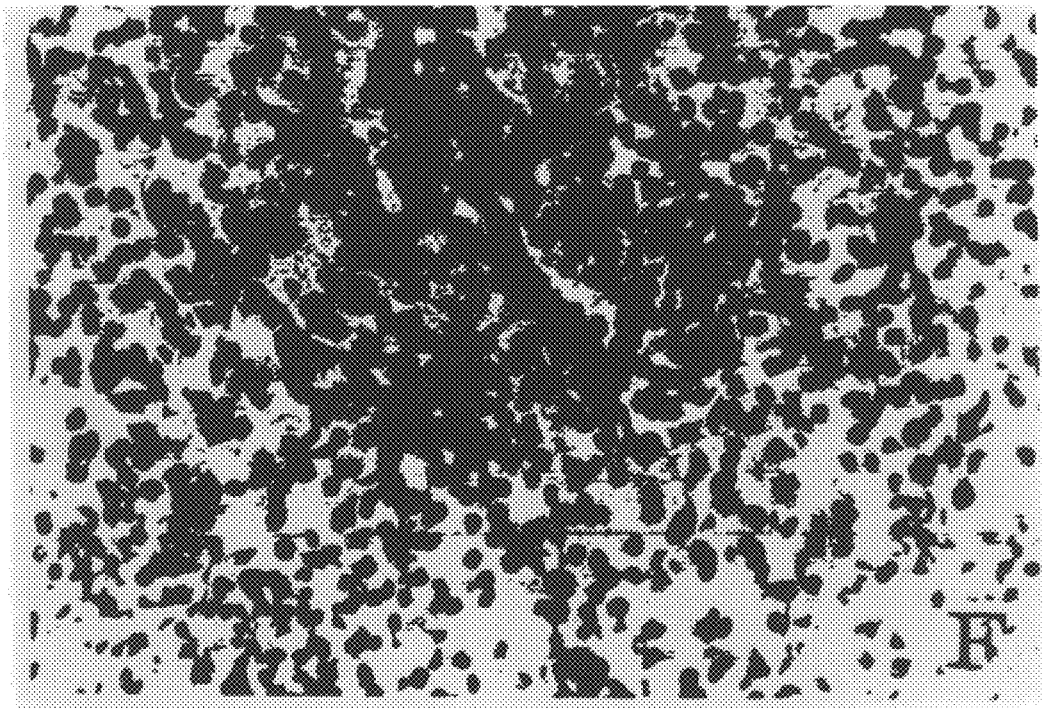
Figure 6G:
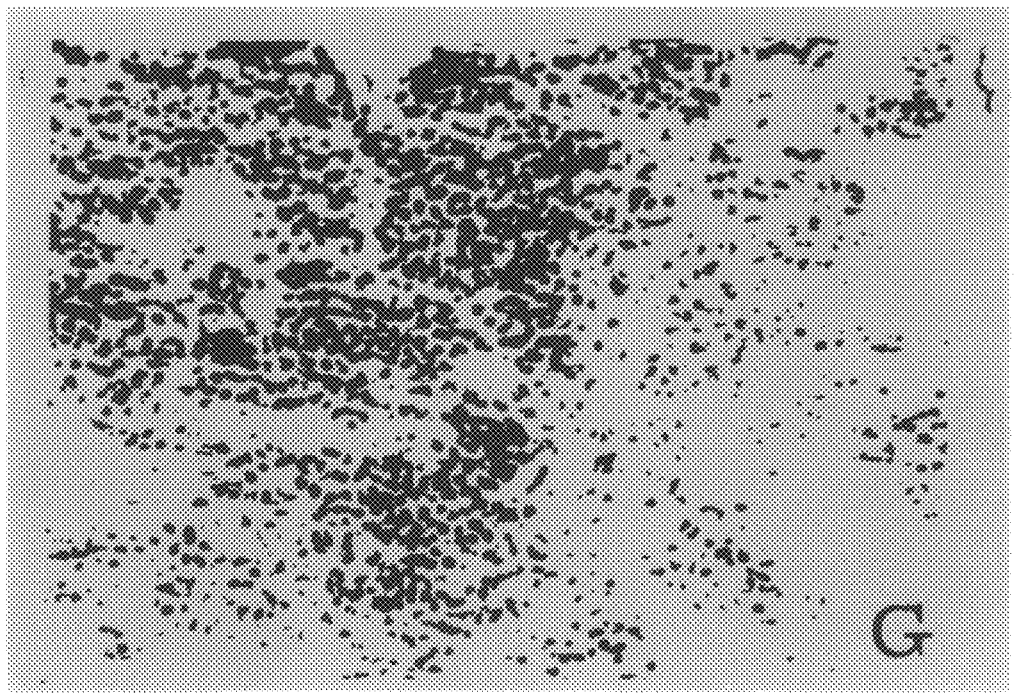
Figure 6H:
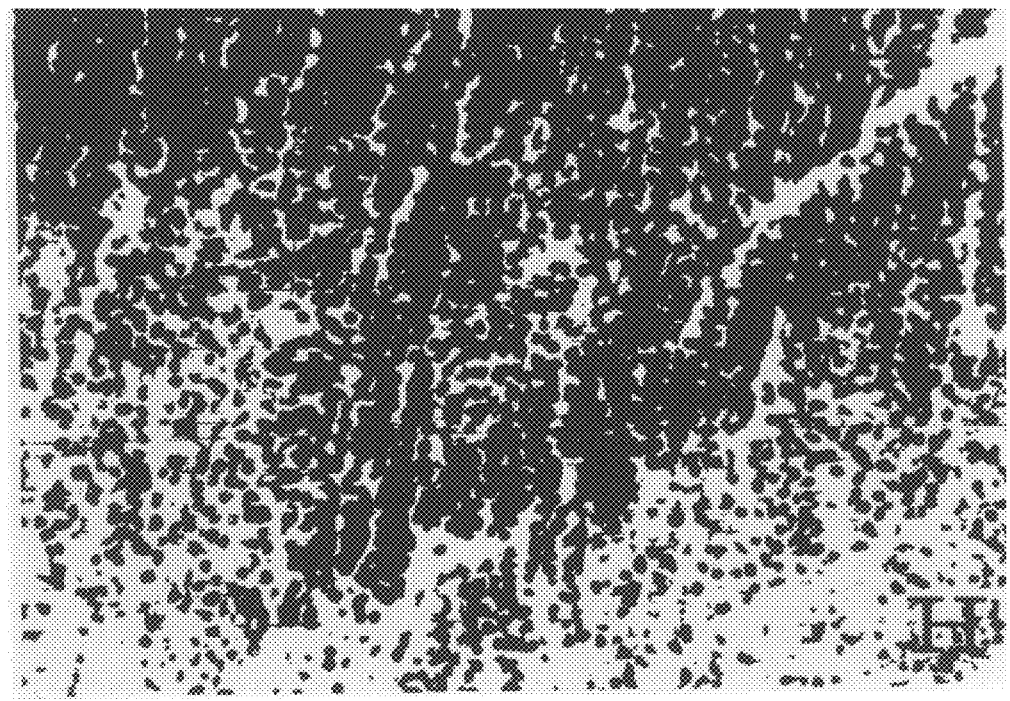

FIG. 6 (6A to 6H) are photographs of kidney sections of the different groups of animals, showing the histological effects, if any, of the different compositions administered to them. FIG. 6A—normal kidney cortex from saline-treated mice (X160); FIG. 6B—cyclosporin and human serum albumin-treated mice (X250); FIG. 6C—cyclosporin and transferrin-treated mice (X250); FIG. 6D—cyclosporin and human serum albumin-treated mice (X250); FIG. 6E—cyclosporin and human serum albumin-treated mice (X250); FIG. 6F—cyclosporin and transferrin-treated mice (X250); FIG. 6G—thymus cortex of cyclosporin and human serum albumin-treated mice (X250); FIG. 6H—thymus cortex cyclosporin and transferrin-treated mice (X250).

DETAILED DESCRIPTION OF PREFERRED EMBODIMENTS

1° Prospective Activity of Human Transferrin (Tf) on the Survival Rate and on the Immunolymphatic Organs of Chemically Immunosuppressed Mice The results of 4 similar experiments, in mice subject to an immunosuppressive treatement with an immunosuppressor (IS), cyclophosphamide, are illustrated in FIGS. 1 and 2. They are expressed in percentages of death as compared to non-immunosuppressed controls.

BALB/C and C57BL/6 mice were injected introperitoneally with 100 (C57BL/6) to 200 mg/kg (BALB/C) of cyclophosphamide (CY, ENDOXAN) on day 0 and again on day 1 with the same dose.

Group 1 (Gr. 1:33 animals) was treated daily for 5 to 15 days intraperitoneally from day 3 with 200 μg/day/mouse of human transferrin (Tf) purified from individual plasma or from plasma pool (SCLAVO SpA, Siena, Italy). control group 2 (Gr. 2:14 animals) was similarly treated with human serum albumin(HSA). Control group 3 of FIG. 1 (Gr. 3:19 animals) was also immunosuppressed but left untreated. But group 3 of FIG. 2 were normal, untreated mice.

As can be seen, Tf protected to a large extent the mice from toxic death (FIG. 1) and corrected and largely prevented the effects of drug toxicity leading to a temporary atrophy of the thymus and to reduction of peripheral blood lymphocytes (FIG. 2).

2° Human Transferrin (Tf) Prevents Kidney Damage (FIG. 3) and Corrects the Toxic Effects (FIGS. 4 and 5) in Mice Treated Chronically with Cyclosporin (CsP)

The results are illustrated in FIGS. 3, 4 and 5.

BALB/C mice (8–12 animals/group) were injected daily subcutaneously for 10 days and later at alternative days until day 35 with different doses (5, 15 and 30 mg/kg) of cyclosporine A and, intraperitoneally, with 200 μg of human transferrin or human serum albumin (HSA) purified from a human plasma pool, (FIG. 3, groups 3, 4, 5, 6, 7, 8). Control group 2 was similarly injected with diluent (saline), while control group 1 was left untreated.

As can be seen, Tf reduces and prevents renal damage as expressed by increased renal weight (oedema, nephrosis, hyperplasia, hypertrophy) measured by renal/body weight ratio (FIG. 3). Treatment of CsP-treated mice with Tf also remarkably normalizes thymus size (FIG. 4) and also stimulates a reconstitution of lymphocyte number in the peripheral blood (FIG. 5).

3° Light Microscopy Analysis of the Prevention and Cure of Cyclosporin-induced Kidney and Thymus Damage by Human Transferrin in Mice The results are illustrated in FIGS. 6 (A–H).

Adult BALB/C female mice were injected daily sc with 30 mg/kg cyclosporin A (SANDIMMUN SANDOZ, Basel, Switzerland). At the same time they were also injected daily ip with human transferrin from a plasma pool (3000 donors pool from the USA) purified by SCLAVO SpA, R. D. Hemoderivatives, Siena, Italy) at the dose of 200 μg/mouse/day (purity over 95%). The treatment was continued until day 30. Control groups were either treated with the same dosage of crystalline human serum albumin (HSA) or with diluent only (saline, no cyclosporine). The enlargement rates are indicated by the numbers which are next to "X", in the sentences which follow.

6A) Normal kidney cortex from saline treated mice. Normal glomeruli and tubules, X160.

6B) Cyclosporine and human serum albumin-treated mice. Notice the kidney epithelium damage, nephrosis, oedema, tubular disruption and dystrophy, X250.

6C) Cyclosporine and transferrin-treated mice. The prevention of kidney epithelium damage in the presence of transferrin must be noticed. The kidney structure and cellularity appears normal. Neither damage or dystrophy of tubules nor oedema can be seen, X250.

6D) cyclosporine and human serum albumin-treated mice. The kidney epithelium damage, the nephrotic syndrome and tubular dystrophy are noticed, X250.

6E) In cyclosporin and HSA-treated mice, the marked tubular damage with tubular dystrophy and oedema consequent to the administration of cyclosporin must be noticed, X250.

6F) Cyclosporin and transferrin-treated mice. Transferrin prevents kidney damage, as shown by normal kidney structure and absence of glomeruli and tubules damage, X250.

6G) Thymus cortex of cyclosporine and human serum albumin-treated mice. The severe depletion of thymocytes in the cortex resulting in atrophy and shrinkage of the thymus must be noticed, X250.

6H) Thymus cortex of cyclosporine and transferrin-treated mice. The maintenance of a normal cortex with packed thymocytes is noticed. The thymus weight, size and structure are maintained too (see tables), X250.

What is claimed is:

1. A drug composition comprising cyclosporin and pooled transferrin, wherein said cyclosporin is not bound, not linked, or not coupled to said pooled transferrin.

2. The drug composition according to claim 1, wherein said transferrin is a human transferrin.

3. A drug composition comprising (i) a cyclosporin which has a cytotoxic effect on a patient to which said agent is administered and (ii) a pooled transferrin in an amount effective to reduce or eliminate the cytotoxic effect of said cyclosporin, when administered to a patient, wherein said cyclosporin is not bound, not linked, or not coupled to said pooled transferrin.

4. The drug composition according to claim 3, wherein said transferrin is a human transferrin.

5. A method for producing an eutrophic drug composition comprising formulating a mixture of a pooled transferrin and cyclosporin wherein said cyclosporin is not bound, not linked or not coupled to said pooled transferrin.

* * * * *